(12) United States Patent
Delfort et al.

(10) Patent No.: US 8,921,602 B2
(45) Date of Patent: Dec. 30, 2014

(54) METHOD FOR SYNTHESISING BIS[3-(N,N-DIALKYLAMINO)PROPYL]ETHERS

(71) Applicant: IFP Energies nouvelles, Rueil-Malmaison Cedex (FR)

(72) Inventors: Bruno Delfort, Paris (FR); Dominique Le Pennec, Orgerus (FR); Julien Grandjean, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 14/361,307

(22) PCT Filed: Oct. 18, 2012

(86) PCT No.: PCT/FR2012/000424
§ 371 (c)(1),
(2), (4) Date: May 29, 2014

(87) PCT Pub. No.: WO2013/079815
PCT Pub. Date: Jun. 6, 2013

(65) Prior Publication Data
US 2014/0336416 A1    Nov. 13, 2014

(30) Foreign Application Priority Data
Nov. 30, 2011  (FR) ..................................... 11 03655

(51) Int. Cl.
    *C07C 213/02*    (2006.01)
(52) U.S. Cl.
    CPC .................................. *C07C 213/02* (2013.01)
    USPC .......................................... 564/508; 564/511
(58) Field of Classification Search
    None
    See application file for complete search history.

(56) References Cited

U.S. PATENT DOCUMENTS

| 2,816,130 | A |  | 12/1957 | Selcer et al. |
| 3,480,675 | A |  | 11/1969 | Poppelsdorf |
| 4,247,482 | A |  | 1/1981  | Poppelsdorf |
| 4,313,004 | A |  | 1/1982  | Kluger et al. |
| 4,965,362 | A |  | 10/1990 | Merger et al. |
| 6,576,794 | B2 | * | 6/2003 | Fukushima et al. .......... 564/292 |

FOREIGN PATENT DOCUMENTS

| DE | 2746751 A1 | 4/1978 |
| FR | 879788 A   | 3/1943 |

OTHER PUBLICATIONS

J. Fakstorp, et al: "Bifunctional Amines and Ammonium Compounds, VI.* Further Homologs and Analogs of bis-Choline Ether Salts," Acta Chemica Scandinavica 11 (1957) pp. 1698-1705.
J Fakstorp, et al: "Bifunctional Amines and Ammonium Compounds, IV.* Higher Bis-dialkylamino Etithers and Their quaternary Ammonium Salts," Acta Chemica Scaninavica (1954). pp. 350-353.
P.F. Wiley: "Di-(y-aminoproply) Ether," J. Am. Chem. Soc., (1946), p. 1867.
O.F. Wiedman, et al: "Some Amine Derivatives of Acrylonitrile," J. Am. Chem. Soc., (1945), pp. 1194-1196.

* cited by examiner

*Primary Examiner* — Brian J Davis
(74) *Attorney, Agent, or Firm* — Antonelli, Terry, Stout & Kraus, LLP.

(57) ABSTRACT

The invention relates to an improved method for synthesizing bis[3-(N,N-dialkylamino)propyl]ethers from acrylonitrile, comprising the following reactions:

first addition reaction of a water molecule and an acrylonitrile molecule to produce 3-hydroxypropionitrile (reaction 1), second addition reaction of a 3-hydroxypropionitrile molecule obtained by reaction 1 and an acrylonitrile molecule to produce bis(2-cyanoethyl)ether (reaction 2), hydrogenation reaction of the bis(2-cyanoethyl)ether to conduct a reduction of the nitrile functions to primary amine functions in order to produce bis(3-aminopropyl) ether (reaction 3), aminoalkylation reaction of the bis(3-aminopropyl)ether to produce bis[3-(N,N-dialkylamino)propyl]ether (reaction 4).

7 Claims, 1 Drawing Sheet

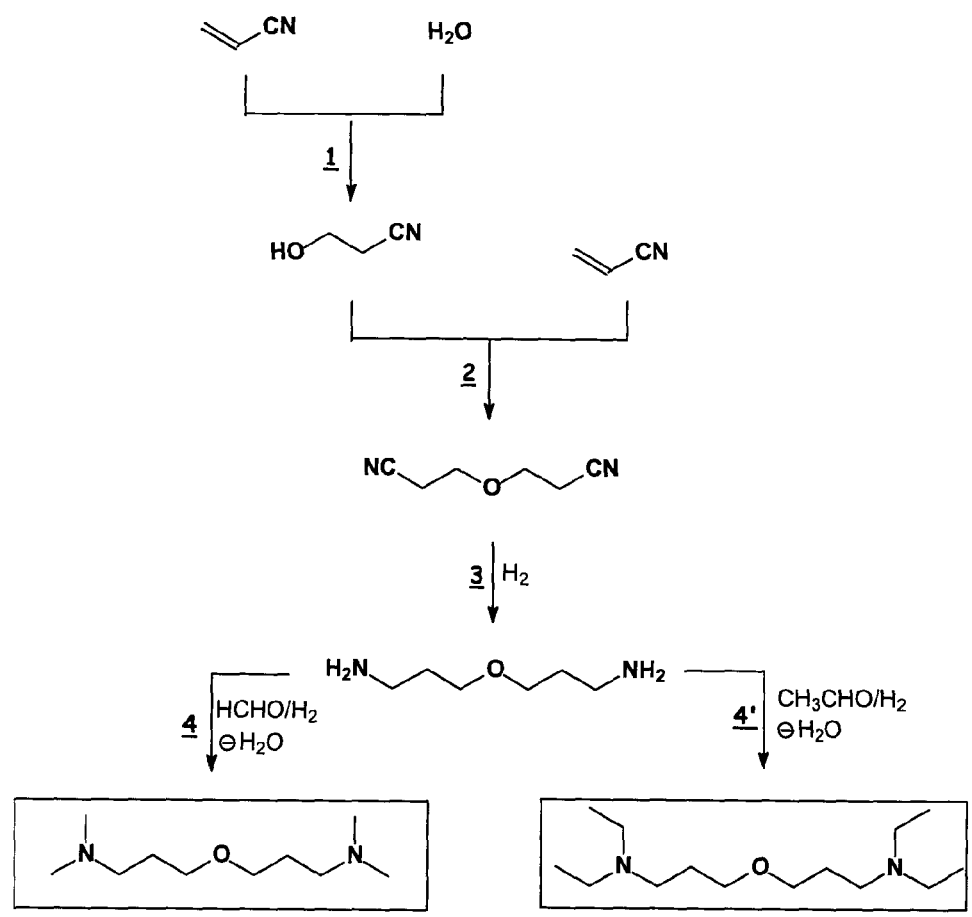

METHOD FOR SYNTHESISING BIS[3-(N,N-DIALKYLAMINO)PROPYL]ETHERS

FIELD OF THE INVENTION

The invention relates to the synthesis of tertiary ether diamines.

CONTEXT

Tertiary ether diamines belonging to the bis[3-(N,N-dialkylamino)alkyl]ether family can be of interest for various applications.

Among these, bis[3-(N,N-dialkylamino)ethyl]ethers have aroused great interest, notably bis[3-(N,N-dimethylamino) ethyl]ether or 1,2-bis(N,N-dimethylaminoethoxy)ethane.

On the other hand, tertiary ether diamines belonging to the bis[3-(N,N-dialkylamino)propyl]ether family have been much less studied. They can also be of interest for various applications.

Tertiary ether diamines belonging to the bis[3-(N,N-dialkylamino)propyl]ether family can be advantageously used for example for deacidizing acid gases, whether natural gas or combustion fumes gas. Acid gas deacidizing is understood to be the reduction in the proportion of acid compounds such as $H_2S$, $CO_2$, COS, $CS_2$, in these gases.

Tertiary ether diamines belonging to the bis[3-(N,N-dialkylamino)propyl]ether family can go into formulations leading to polymers, notably polyurethanes.

Tertiary ether diamines belonging to the bis[3-(N,N-dialkylamino)propyl]ether family can be molecular precursor compounds with applications in other fields in chemistry.

Among the tertiary ether diamines belonging to the bis[3-(N,N-dialkylamino)propyl]ether family, two molecules can be of particular interest:

Bis[3-(N,N-dimethylamino)propyl]ether:

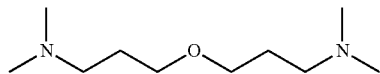

and bis[3-(N,N-diethylamino)propyl]ether:

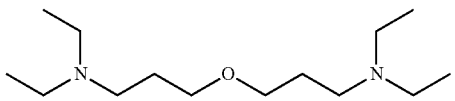

BACKGROUND OF THE INVENTION

The prior art on the synthesis of bis[3-(N,N-dialkylamino) propyl]ethers is much less abundant than on the synthesis of bis[3-(N,N-dialkylamino)ethyl]ethers. The synthesis of the latter is mainly based on the chemistry of ethylene oxide, which is the precursor of the ethoxyethyl pattern connecting the two amine functions.

The propoxypropyl pattern that connects the two amine functions of bis[3-(N,N-dialkylamino)ethyl]ethers cannot be based on the chemistry of propylene oxide that would lead to bis[2-(N,N-dialkylamino)propyl]ethers and not bis[3-(N,N-dialkylamino)propyl]ethers as desired. In fact, few studies on the synthesis of bis[3-(N,N-dialkylamino) propyl]ethers are available.

The synthesis of bis[3-(N,N-dialkylamino)propyl]ethers is described by J. Fakstorp et al. The synthesis of bis[3-(N,N-dimethylamino)propyl]ether is described in Acta. Chem. Scand., 11 (1957), 1698-1705, by reaction of 3-(dimethylamino)-propanol with 1-chloro-3-(dimethylamino)-propane. This reaction results from the condensation of the alkaline alcoholate, sodium alcoholate for example, of the previously prepared 3-(dimethylamino)-propanol on 1-chloro-3-(dimethylamino)-propane. By doing so, for each mole of bis[3-(N,N-dimethylamino)propyl]ether formed, one mole of alkaline chloride, sodium chloride for example, is produced.

The same author describes in Acta. Chem. Scand., 8 (1954), 350-353, the synthesis of bis[3-(N,N-diethylamino) propyl]ether by reaction of 3-(diethylamino)-propanol with 1-chloro-3-(diethylamino)-propane under similar conditions.

U.S. Pat. No. 3,480,675 (1969) claims an improvement of this operating mode by conducting a single stage in the presence of a base allowing in-situ generation of 3-(dialkylamino)-propanol alcoholate. Here also, one mole of alkaline chloride, sodium chloride for example, is produced per mole of bis[3-(N,N-dialkylamino)propyl]ether.

These synthesis routes use 1-chloro-3-(dimethylamino)-propane or 1-chloro-3-(diethylamino)-propane as the reagent. These molecules result from the chlorination of 3-(dimethylamino)-propanol or 3-(diethylamino)-propanol. This reaction is carried out using a chlorinating agent that can be, for example, hydrochloric acid, thionyl chloride, phosphorus trichloride or phosphorus pentachloride. These chlorinating agents are corrosive and sometimes generate by-products such as sulfur dioxide in the case of thionyl chloride. Their large-scale industrial use is therefore not desirable.

U.S. Pat. No. 4,247,482 (1981) provides a synthesis route where the 3-(dialkylamino)-propanol is first converted to sodium alcoholate by reaction with a base, then converted by reaction with sulfur trioxide to an intermediate product 3-(dialkylamino)-propane-1-sodium sulfate, which by condensation with the sodium alcoholate of 3-(dialkylamino)-propanol leads to bis[3-(N,N-dialkylamino)propyl]ether by generating an equimolar proportion of sodium sulfate.

Salt formation is inevitable in view of the synthesis routes described by the prior art. In all the cases described, one mole of salt per mole of bis[3-(N,N-dialkylamino)propyl]ether is inevitably formed. The generation of salts in large amounts, which have to be removed later or which are difficult to manage, has become incompatible with the development of modern industrial chemical processes. Thus, the technologies described in the prior art are today hardly compatible with the large-scale industrial production of bis[3-(N,N-dialkylamino)propyl]ether.

DESCRIPTION OF THE INVENTION

It has been found that it is possible to prepare bis[3-(N,N-dialkylamino)propyl]ethers according to a procedure that generates no salt and that is compatible with industrial development.

This procedure involves a sequence of four reactions where only one (the last one) generates a co-product that is water.

The sequence of these four reactions can be conducted in three or four stages.

The starting product used (precursor) is acrylonitrile, which is an industrial molecule, a polymer precursor, widely available worldwide and at a low cost.

SUMMARY OF THE INVENTION

The invention relates to a method for synthesizing bis[3-(N,N-dialkylamino)propyl]ethers from acrylonitrile, comprising the following reactions:

first addition reaction of a water molecule and an acrylonitrile molecule to produce 3-hydroxypropionitrile (reaction 1), second addition reaction of a 3-hydroxypropionitrile molecule obtained by reaction 1 and an acrylonitrile molecule to produce bis(2-cyanoethyl)ether (reaction 2), hydrogenation reaction of the bis(2-cyanoethyl)ether to conduct a reduction of the nitrile functions to primary amine functions in order to produce bis(3-aminopropyl)ether (reaction 3), aminoalkylation reaction of the bis(3-aminopropyl)ether to produce bis[3-(N,N-dialkylamino)propyl]ether (reaction 4).

In one embodiment, the first and second addition reactions 1 and 2 are carried out in situ in a single stage.

In another embodiment, the first and second addition reactions 1 and 2 are carried out in two successive stages.

In this case, advantageously, the second addition reaction is conducted in the presence of either excess 3-hydroxypropionitrile or excess acrylonitrile.

Advantageously, the first addition reaction is conducted in the presence of either excess acrylonitrile or excess water.

Advantageously, the aminoalkylation reaction is carried out by catalytic reductive alkylation of the bis(3-aminopropyl)ether by means of an aldehyde in the presence of hydrogen and of a hydrogenation catalyst.

Preferably, the bis[3-(N,N-dialkylamino)propyl]ether produced is bis[3-(N,N-dimethyl-amino)propyl]ether or bis[3-(N,N-diethylamino)propyl]ether.

DETAILED DESCRIPTION

List of the Figures

FIG. 1 illustrates the invention by way of non-limitative example.

FIG. 1 shows the method of synthesizing bis[3-(N,N-dimethylamino)propyl]ether (left lane) and bis[3-(N,N-diethylamino)propyl]ether (right lane) from acrylonitrile as the starting product, comprising the stages of the method according to the invention.

Description of FIG. 1

FIG. 1 describes the synthesis method according to the invention using acrylonitrile as the starting product for producing bis[3-(N,N-dimethylamino)propyl]ether (left lane) or bis[3-(N,N-diethylamino)propyl]ether (right lane).

Addition Reactions (1 and 2)

Reaction 1: Hydrolysis by Water and Acrylonitrile Addition

The first stage consists in adding a water molecule and an acrylonitrile molecule so as to obtain 3-hydroxypropionitrile (reaction 1) according to a known reaction.

Reaction 2: Addition of the Product of Stage 1 with an Acrylonitrile Molecule

A 3-hydroxypropionitrile molecule reacts in turn with an acrylonitrile molecule, thus leading to bis(2-cyanoethyl)ether (reaction 2).

Addition reactions (1) and (2) can be conducted in two successive stages (1) and (2) or in situ in a single stage (1+2).

These reactions are addition reactions and they generate no by-product.

They can be promoted in the presence of bases.

In cases where reactions 1 and 2 are carried out in two successive stages, it may be advantageous in reaction 1 to use either excess acrylonitrile or excess water. Either of these excess reagents is easily separated, for example by distillation at the end of reaction 1, and recycled to the process.

It may also prove advantageous in reaction 2 to use either excess acrylonitrile or excess 3-hydroxypropionitrile. Either of these excess reagents is separated for example by distillation at the end of reaction 2 and recycled to the process.

In cases where reactions 1 and 2 are conducted in situ in a single stage, it may be advantageous to use either excess acrylonitrile, which is easily separated later and recycled to the process, or excess water that leads to the additional formation of 3-hydroxypropionitrile that is easily separated later and recycled to the process. Either of these excess reagents can be easily separated for example by distillation at the end of the stage.

The boiling-point temperatures of acrylonitrile, water and 3-hydroxypropionitrile are 77° C., 100° C. and 228° C. respectively at atmospheric pressure, and that of bis(2-cyanoethyl)ether is 110° C. under 0.5 mm mercury. Stages of separating possible excesses of one or more reagents can therefore be easily considered by distillation. Consequently, in these stages, the possible use of one or more of the reagents in excess to reach maximum conversion under advantageous time and temperature conditions is fully compatible with the method described.

These reactions are notably described in U.S. Pat. Nos. 2,382,036, 2,448,979 and 2,816,130 describing the addition of water and acrylonitrile leading to 3-hydroxypropionitrile and bis(2-cyanoethyl)ether. U.S. Pat. No. 4,965,362 describes the presence of bases such as ammonium salts to conduct these reactions.

The 13C NMR (CDCl3) characteristics of 3-hydroxypionitrile are as follows:
57.4 ppm: HO—CH2-CH2-CN
21.4 ppm: HO—CH2-CH2-CN
118.9 ppm: HO—CH2-CH2-CN The H NMR (CDCl3) characteristics of 3-hydroxypropionitrile are as follows:
3.4 ppm: HO—CH2-CH2-CN
3.85 ppm: HO—CH2-CH2-CN
2.61 ppm: HO—CH2-CH2-CN The 13C NMR (CDCl3) characteristics of bis(2-cyanoethyl)ether are as follows:
118.1 ppm: NC═CH2-CH2-O—CH2-CH2-CN
18.8 ppm: NC═CH2-CH2-O—CH2-CH2-CN
67.7 ppm: NC═CH2-CH2-O—CH2-CH2-CN The H NMR (CDCl3) characteristics of bis(2-cyanoethyl) ether are as follows:
2.65 ppm: NC═CH2-CH2-O—CH2-CH2-CN
3.74 ppm: NC═CH2-CH2-O—CH2-CH2-CN Reduction Reaction of the Nitrite Functions by Hydrogenation (Reaction 3)

The bis(2-cyanoethyl)ether obtained after reaction 2 is hydrogenated so as to lead to bis(3-aminopropyl)ether according to the known reaction of reduction of the nitrile functions to primary amine functions (reaction 3). This reaction can be conducted with any means known to the person skilled in the art in accordance with organic chemistry.

It can be conducted for example by means of a suitable hydride such as the mixed lithium aluminium hydride.

Preferably, the reduction of the nitrile functions to primary amine functions is carried out in the presence of hydrogen, or in the presence of hydrogen and ammonia by means of a suitable catalyst such as nickel derivatives for example.

This reaction is a reaction of addition of hydrogen to the nitrile function and it generates no by-product. Preferably, the reaction is conducted at a temperature ranging between 80° C. and 190° C., preferably between 80° C. and 130° C., and at a pressure ranging between 5 and 220 bars, preferably between 20 and 150 bars.

Patent FR-879,788 (1942) describes the hydrogenation of β,β'-dicyanodiethyl ether in the presence of a cobalt-based catalyst and ammonia at a temperature ranging from 90° C. to 100° C., leading to bis(3-aminopropyl)ether.

O. F. Wiedman et al. describe in J. Am. Chem. Soc., (1945), p. 1194, a general method for hydrogenation of dicyanoethyl ether to diaminopropyl ether in the presence of Raney nickel and ammonia between 50 and 150 bars, at a temperature ranging from 80° C. to 125° C.

This reaction is also described by P. F. Wiley in J. Am. Chem. Soc., (1946), p. 1867, at a temperature ranging from 100° C. to 110° C. in the presence of ammonia, methanol and Raney nickel.

U.S. Pat. No. 4,313,004 describes the reduction of various dicyanoglycols in the presence of ammonia and of a cobalt-based catalyst between 90° C. and 160° C.

This reaction is also described in patent FR-2,367,736 (1977) that claims the hydrogenation of bis(2-cyanoethyl) ether between 100° C. and 175° C., at a pressure ranging between 34 and 207 bars, in a cyclic ether solvent in the presence of ammonia and a nickel or cobalt-based catalyst.

The 13C NMR (CDCl3) characteristics of bis(3-aminopropyl)ether are as follows:

39.7 ppm: H2N—CH2-CH2-CH2-O—CH2-CH2-CH2-NH2

33.8 ppm: H2N—CH2-CH2-CH2-O—CH2-CH2-CH2-NH2

69.1 ppm: H2N—CH2-CH2-CH2-O—CH2-CH2-CH2-NH2

The H NMR (CDCl3) characteristics of bis(3-aminopropyl)ether are as follows:

1.13 ppm: H2N—CH2-CH2-CH2-O—CH2-CH2-CH2-NH2

2.79 ppm: H2N—CH2-CH2-CH2-O—CH2-CH2-CH2-NH2

1.17 ppm: H2N—CH2-CH2-CH2-O—CH2-CH2-CH2-NH2

33.49 ppm: H2N—CH2-CH2-CH2-O—CH2-CH2-CH2-NH2

Aminoalkylation Reaction (Reaction 4)

Finally, the bis(3-aminopropyl)ether is converted to bis[3-(N,N-dimethyl-amino)propyl]ether or bis[3-(N,N-diethylamino)propyl]ether according to an aminoalkylation reaction that is, in the case of FIG. 1, a methylation or an ethylation (reaction 4 or 4').

These aminoalkylations can be carried out using any method permitted by organic chemistry and known to the person skilled in the art.

The so-called Eschweiler-Clarke methylation reaction that requires a mixture of formaldehyde and formic acid can be mentioned by way of example.

The Leuckart reaction that uses a ketone or an aldehyde and an ammonium formiate can also be mentioned.

Preferably, aminoalkylation is carried out by the reaction known as catalytic reductive alkylation of amines using an aldehyde, formaldehyde or acetaldehyde for example, in the presence of hydrogen and of a suitable catalyst selected from among hydrogenation catalysts such as, by way of (non-limitative) example, platinum on charcoal, palladium on charcoal or nickel, copper or chromium derivatives, such as Raney nickel for example. Catalytic reductive alkylation reactions of amines afford, among other things, the advantage of being fast, selective and of generating only water (condensation) as a by-product. They are widely used in industrial methods for production of alkylamines, such as methylamines or ethylamines, and they are compatible with technologies used industrially.

More generally, the aminoalkylation reaction uses an aldehyde or a ketone, and it is advantageously conducted at a temperature ranging between ambient temperature and 200° C. for example, preferably at a pressure ranging between atmospheric pressure and 80 bars. The experimental conditions are highly dependent on the nature of the catalytic system used.

The methylation of bis(3-aminopropyl)ether to bis[3-(N,N-dimethylamino)propyl]ether can for example be carried out in an autoclave reactor by reaction with excess formaldehyde under a hydrogen pressure of 20 bars at 120° C. in 3 hours, in the presence of a palladium-on-charcoal catalyst.

The ethylation of bis(3-aminopropyl)ether to bis[3-(N,N-diethylamino)propyl]ether can for example be carried out using the same procedure, but by replacing formaldehyde by acetaldehyde.

The 13C NMR (CDCl3) characteristics of bis[3-(N,N-dimethylamino)propyl]ether are as follows:

13C-RMN(CDCl3):

27.3 ppm: (CH3)2N—CH2-CH2-CH2-O—CH2-CH2-CH2-N(CH3)2

44.7 ppm: (CH3)2N—CH2-CH2-CH2-O—CH2-CH2-CH2-N(CH3)2

55.9 ppm: (CH3)2N—CH2-CH2-CH2-O—CH2-CH2-CH2-N(CH3)2

68.2 ppm: (CH3)2N—CH2-CH2-CH2-O—CH2-CH2-CH2-N(CH3)2

The 13C NMR (CDCl3) characteristics of bis[3-(N,N-diethylamino)propyl]ether are as follows:

13C-RMN (CDCl3):

11.3 ppm: (CH3-CH2)2N—CH2-CH2-CH2-O—CH2-CH2-CH2-N(CH2-CH3)2

27.1 ppm: (CH3-CH2)2N—CH2-CH2-CH2-O—CH2-CH2-CH2-N(CH2-CH3)2

46.3 ppm: (CH3-CH2)2N—CH2-CH2-CH2-O—CH2-CH2-CH2-N(CH2-CH3)2

49.1 ppm: (CH3-CH2)2N—CH2-CH2-CH2-O—CH2-CH2-CH2-N(CH2-CH3)2

68.5 ppm: (CH3-CH2)2N—CH2-CH2-CH2-O—CH2-CH2-CH2-N(CH2-CH3)2

Variants of the Synthesis Method According to the Invention

A variant of the method according to the invention can involve acrylamide instead of acrylonitrile as the starting product, the stages of the synthesis method according to the invention being as described above: the acrylamide hydrolysis stage then leads to propanamide, 3,3'-oxybis that is hydrogenated to bis(3-aminopropyl)ether, then alkylated, for example methylated or ethylated as described above.

Similarly, one may consider using N,N-dimethylacrylamide or N,N-diethylacrylamide instead of acrylonitrile. The hydrolysis stage then leads to N,N-dimethyl-propanamide,3,3'-oxybis or N,N-diethylpropanamide,3,3'-oxybis. Finally, a stage of hydrogenation of the amide functions, followed by alkylation or not, leads to the diamines of the invention.

Application of the Synthesis Method According to the Invention

The synthesis method according to the invention can be used to produce tertiary ether diamines belonging to the bis [3-(N,N-dialkylamino)propyl]ether family. They can be advantageously used for example for deacidizing acid gases, whether natural gas or combustion fumes gas. Acid gas deacidizing is understood to be the reduction in the proportion of acid compounds such as $H_2S$, $CO_2$, $COS$, $CS_2$, in these gases.

Among the tertiary ether diamines belonging to the bis[3-(N,N-dialkylamino)propyl]ether family and produced by means of the synthesis method according to the invention, two molecules can be of particular interest for acid gas deacidizing:

Bis[3(N,N-dimethylamino)propyl]ether

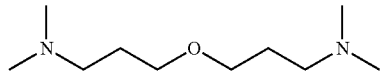

and bis[3-(N,N-diethylamino)propyl]ether:

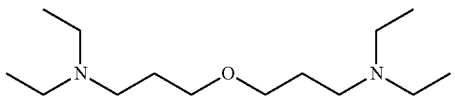 [SMILES: CCN(CC)CCCOCCCN(CC)CC]

The invention claimed is:

1. A method for synthesizing bis[3-(N,N-dialkylamino)propyl]ethers from acrylonitrile, comprising the following reactions:
   first addition reaction of a water molecule and an acrylonitrile molecule to produce 3-hydroxypropionitrile (reaction 1),
   second addition reaction of a 3-hydroxypropionitrile molecule obtained by reaction 1 and an acrylonitrile molecule to produce bis(2-cyanoethyl)ether (reaction 2),
   hydrogenation reaction of the bis(2-cyanoethyl)ether to conduct a reduction of the nitrile functions to primary amine functions in order to produce bis(3-aminopropyl)ether (reaction 3),
   aminoalkylation reaction of the bis(3-aminopropyl)ether to produce bis[3-(N,N-dialkylamino)propyl]ether (reaction 4).

2. A synthesis method as claimed in claim 1, wherein the first and second addition reactions 1 and 2 are carried out in situ in a single stage.

3. A synthesis method as claimed in claim 1, wherein the first and second addition reactions 1 and 2 are carried out in two successive stages.

4. A synthesis method as claimed in claim 3, wherein the second addition reaction is conducted in the presence of either excess 3-hydroxypropionitrile or excess acrylonitrile.

5. A synthesis method as claimed in claim 1, wherein the first addition reaction is conducted in the presence of either excess acrylonitrile or excess water.

6. A method as claimed in claim 1, wherein the aminoalkylation reaction is carried out by catalytic reductive alkylation of the bis(3-aminopropyl)ether by means of an aldehyde in the presence of hydrogen and of a hydrogenation catalyst.

7. A method as claimed in claim 1, wherein the bis[3-(N,N-dialkylamino)propyl]ether produced is bis[3-(N,N-dimethylamino)propyl]ether or bis[3-(N,N-diethylamino)propyl]ether.

* * * * *